(12) United States Patent
Faizal et al.

(10) Patent No.: US 9,278,117 B2
(45) Date of Patent: Mar. 8, 2016

(54) COMPOSITION AND METHOD FOR THE SAFE AND EFFECTIVE INHIBITION OF PANCREATIC LIPASE IN MAMMALS

(71) Applicant: Bio Actives Japan Corporation, Tokyo (JP)

(72) Inventors: Mohamed Faizal, Tokyo (JP); Hiroshi Nishida, Tokyo (JP); Vladimir Badmaev, Staten Island, NY (US)

(73) Assignee: Bio Actives Japan Corporation, Tokyo (JP)

( * ) Notice: Subject to any disclaimer, the term of this patent is extended or adjusted under 35 U.S.C. 154(b) by 0 days.

(21) Appl. No.: 14/390,392

(22) PCT Filed: Apr. 1, 2013

(86) PCT No.: PCT/JP2013/002252
§ 371 (c)(1),
(2) Date: Oct. 2, 2014

(87) PCT Pub. No.: WO2013/150771
PCT Pub. Date: Oct. 10, 2013

(65) Prior Publication Data
US 2015/0056309 A1 Feb. 26, 2015

(30) Foreign Application Priority Data
Apr. 3, 2012 (JP) ................. 2012-084645

(51) Int. Cl.
| | |
|---|---|
| A01N 65/00 | (2009.01) |
| A61K 36/53 | (2006.01) |
| A61K 31/352 | (2006.01) |
| A61K 31/36 | (2006.01) |
| A61K 45/06 | (2006.01) |
| A61K 36/37 | (2006.01) |
| A61K 36/185 | (2006.01) |

(52) U.S. Cl.
CPC ............ *A61K 36/53* (2013.01); *A61K 31/352* (2013.01); *A61K 31/36* (2013.01); *A61K 36/185* (2013.01); *A61K 36/37* (2013.01); *A61K 45/06* (2013.01)

(58) Field of Classification Search
CPC .................................................... A61K 36/00
USPC ..................................................... 424/725
See application file for complete search history.

(56) References Cited

FOREIGN PATENT DOCUMENTS

| | | | |
|---|---|---|---|
| JP | 2000-309533 A | 11/2000 |
| JP | 2001-206893 A | 7/2001 |
| JP | 2004-091464 | 3/2004 |
| JP | 2005-008572 A | 1/2005 |
| JP | 2007-195510 A | 8/2007 |
| JP | 2009-179579 A | 8/2009 |
| JP | 2010-202634 | 9/2010 |

OTHER PUBLICATIONS

Yoshikawa et al. "Salacia reticulata arid Its Polyphenolic Constituents with Lipase Inhibitory and Lipolytic Activities Have Mild Anti-obesity Effects in Rats", Journal of Nutrition, 2002, vol. 132, No. 7, pp. 1819-1824.
Shimoda et al., "Effects of an Aqueous Extract of Salacia reticulata, a Useful Plant in Sri Lanka, on Postprandial Hyperglycemia in Rats and Humans", J. Jpn. Soc. Nutr. Food Sci., vol. 51, pp. 279-287 (1998).
Yoshikawa, 2002, vol. 44, No. 12, pp. 26-30.
Japanese Office Action issued in corresponding application No. 2012-084645 on Nov. 19, 2013.
Japanese Office Action issued in corresponding application No. 2012-084645 on Aug. 5. 2014.
Li Y, et al. Salacia root, a unique Ayurvedic medicine, meets multiple targets in diabetes and obesity, Life Sciences, 2008, vol. 82, No. 21-22, p. 1045-1049.
Filippatos TD, Derdemezis CS, Gazi IF, Nakou ES, Mihailidis DP, Elisaf MS. Orlistat associated adverse effects and drug interactions: a critical review. Drug Suf 2008: 31(1): 53-65)
Badmaev V, Majeed A, Conte A, Parker JE. Diterpene Forskolin (Coleus forskohlii, Benth.): A Possible new compound for reduction of body weight by increasing lean body mass. NutraCos vol. 1, No. 2 (Mar./Apr.); 2002.
Godard MP, Johnson BA, Richmond SR. Body composition and hormonal adaptations associated with forskolin consumption in overweight and obese men, Obes Res Aug. 2005; 13(8): 1335-43.
http://www.fda.gov/Drugs/DrugSafety/PostmarketDrugSafetyinformationforPatientsandProviders/ucm213038.htm.
Ellrichmann M, Kapelle M, Ritter PR, Holst JJ, Herzig KH, Schmidt WE, Schmitz F, Meier JJ. Orlistat inhibition of intestinal lipase acutely increases appetite and attenuates postprandial glucagon-like peptide-1-(7-36-amide-1, cholecystokinin, and peptide YY concentrations. J. Clin Endorinol. Metab. Oct. 2008; 93(10): 3995-8 Epub Jul. 22, 2008.
Duan RD, Erlanson-Albertsson C. Evidence of a stimulatory effect of cyclic AMP on pancreatic lipase and colipase synthesis in rats. Scand J Gastroenterol. Aug. 1992; 27(8): 644-8.
WIPO/Japanese Patent Office, International Search Report, PCT/JP2013/002252 mailed Jun. 25, 2013.

*Primary Examiner* — Michael Meller
(74) *Attorney, Agent, or Firm* — Carter, DeLuca, Farrell & Schmidt, LLP

(57) ABSTRACT

Provided are a composition and method for the safe and effective inhibition of pancreatic lipase in humans and other mammals. Provided is a composition which contains extracts of one or more of *Coleus forskohlii, Salacia reticulata*, and *Sesamum indicum*, and which is administered orally to humans and other mammals in a nutritionally or pharmacologically effective amount. Further provided is a method for producing said composition.

7 Claims, 1 Drawing Sheet

COMPOSITION AND METHOD FOR THE SAFE AND EFFECTIVE INHIBITION OF PANCREATIC LIPASE IN MAMMALS

BACKGROUND OF THE INVENTION

1. Field of the Invention

The present invention relates to a composition for safe and effective inhibition of pancreatic lipase and its use and a method for producing said composition.

2. Description of the Related Art

Digestion and absorption of dietary fat are regulated by the action of pancreatic triglyceride lipase (PTL), and colipase which is a small protein cofactor and is needed by pancreatic lipase for efficient dietary lipid hydrolysis. The enzyme and cofactor are excreted from the pancreas to duodenum. PTL is the primary lipase that hydrolyzes dietary fat molecules in the human duodenum and converts triglyceride substrates to monoglycerides and free fatty acids. The resulting monomers (2 free fatty acids and one 2-monoacylglycerol) are packed into micelle and then absorbed into the lymphatic system by a specialized vessel called a lacteal. Colipase, an enzyme belonging to family of pancreatic lipases, binds to the non-catalytic domain of lipase, and increases stability and hydrophobicity of the binding site. Colipase also prevents the inhibitory effect of various dietary factors on the lipase-catalyzed hydrolysis of dietary long-chain triglycerides.

Blocking the mechanisms of dietary fat digestion and absorption has been utilized in management of obesity. Inhibition of PTL activity with tetrahydrolipostatin (Orlistat/Xenical) and its diluted version, sold over-the-counter under the brand name of "Alli", has been widely used in the pharmacotherapy of obesity. While tetrahydrolipostatin based products have been clinically proven as safe and effective, there are several known side effects and potential side effects of therapy.

The primary side effects of the drug are gastrointestinal tract-related, and include steatorrhea (oily, loose stools with excessive intestinal putrefaction and flatus due to unabsorbed fats reaching the large intestine), fecal incontinence, frequent bowel movements and urgent bowel movements. The potential organ toxicity of tetrahydrolipostatin has been signaled by the U.S. Food and Drug Administration (FDA). On May 26, 2010, the FDA has approved a revised label for tetrahydrolipostatin based drugs to include new safety information about cases of liver injury that have been reported rarely with the use of this medication (Non-Patent Document 1).

The use of tetrahydrolipostatin has been associated with isolated cases of acute kidney injury, possibly due to the fat malabsorption resulting from the excessive inhibition of pancreatic lipase, leading to the formation of soaps of fatty acid with calcium and resulting in increased free oxalate absorption and hyperoxaluria (Non-Patent Document 2).

Absorption of fat-soluble vitamins and other fat-soluble nutrients may be compromised with tetrahydrolipostatin, and thus, supplemental multivitamin containing vitamins A, D, E, K, and beta-carotene should be taken once a day while on tetrahydrolipostatin therapy to prevent the therapy associated vitamin deficiency.

There are also recognized shortfalls of the weight loss mechanism of tetrahydrolipostatin, including increasing appetite and time dependent diminishing drug efficacy occurring after several weeks of treatment. In one study, perception of satiety was significantly decreased in subjects on tetrahydrolipostatin coinciding with the significant decrease in circulating satiety hormones, i.e., CCK, PYY, and GLP-1 in the study subjects (Non-Patent Document 3).

As described above, current generation of pancreatic lipase inhibitors have potentially serious side effects and their efficacy tend to decrease with prolonged use, i.e., tachyphylaxis and increases levels of appetite may cause diminishing their weight loss potential.

PRIOR ART DOCUMENTS

Non-Patent Documents

[Non-Patent Document 1] http://www.fda.gov/Drugs/DrugSafety/PostmarketDrugSafetyInformationforPatientsandProviders/ucm213038.htm

[Non-Patent Document 2] Filippatos T D, Derdemezis C S, Gazi I F, Nakou E S, Mikhailidis D P, Elisaf M S. Orlistat-associated adverse effects and drug interactions: a critical review. Drug Suf 2008; 31(1): 53-65).

[Non-Patent Document 3] Ellrichmann M, Kapelle M, Ritter P R, Holst J J, Herzig K H, Schmidt W E, Schmitz F, Meier J J Orlistat inhibition of intestinal lipase acutely increases appetite and attenuates postprandial glucagon-like peptide-1-(7-36)-amide-1, cholecystokinin, and peptide Y Y concentrations. J Clin Endorinol Metab. 2008 October; 93(10): 3995-8. Epub 2008 Jul. 22.

[Non-Patent Document 4] Badmaev V, Majeed A, Conte A, Parker J E. Diterpene Forskolin (*Coleus forskohlii*, Benth.): A possible new compound for reduction of body weight by increasing lean body mass. NutraCos Vol. 1, No. 2 (March/April); 2002.

[Non-Patent Document 5] Godard M P, Johnson B A, Richmond S R Body composition and hormonal adaptations associated with forskolin consumption in overweight and obese men. Obes Res 2005 August; 13(8): 1335-43.

[Non-Patent Document 6] Duan R D, Erlanson-Albertsson C Evidence of a stimulatory effect of cyclic AMP on pancreatic lipase and colipase synthesis in rats. Scand J Gastroenterol. 1992 August; 27(8): 644-8.

SUMMARY OF THE INVENTION

Problems to be Solved by the Invention

An object of the present invention is to provide a method and a composition for safe and effective inhibition of pancreatic lipase in humans and other mammal and a method for producing said composition.

Means for Solving the Problems

As a result of a devoted investigation, the present inventors have found that each of *Coleus forskohlii* extract (hereinafter also referred to as "CF"), *Salacia reticulata* extract (hereinafter also referred to as "SR"), and *Sesamum indicum* extract (hereinafter also referred to as "SI") has pancreatic lipase inhibition activity. The present inventors also have found that a composition including at least one or more extracts safely and effectively inhibits pancreatic lipase to accomplish the present invention.

Specifically, the present invention provides a composition including at least one or more of the CF extract, the SR extract, and the SI extract. The present invention also provides a method for administering said composition to humans and other mammals in a nutritionally and/or pharmacologically effective amount. The present invention further provides a method for producing said composition.

Effects of the Invention

The present invention provides a composition including at least one or more of the CF extract, the SR extract, and the SI extract for safe and effective inhibition of pancreatic lipase. The composition of the present invention is administered to subjects, so that diminishing of viscera fat, liver fat, triglyceride, appetite, caloric intake, percentage body fat, body weight, waist circumference and/or blood lipid of said subjects and/or prevention of tachyphylaxis of said subjects can be achieved.

BEST MODES FOR CARRYING OUT THE INVENTION

Figure 1:
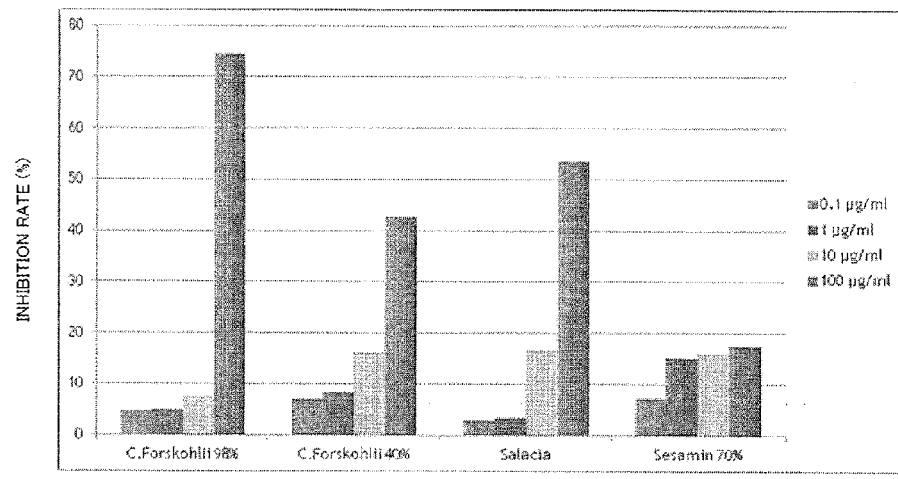
FIG. 1 is a graph illustrating the inhibition rate of pancreatic lipase activity when the CF extract (*C. Forskohlii* 98% or 40%), the SR extract (*Salacia*), or the SI extract (*Sesamin* 70%) is used alone.

The present invention provides a method and a composition for inhibiting pancreatic lipase activity in humans and other mammals to accomplish safe and effective control of digestive fatty acids excessive accumulation in organs (liver fat), viscera fat (abdominal fat) and peripheral tissue in the form of white (storage) fat. The present invention also provides a method for producing said composition.

The composition of the present invention includes one or more extracts selected from the group consisting of the CF extract standardized for forskolin, the SR extract standardized for half maximal inhibitory concentration ($IC_{50}$) for α-glucosidase inhibition and for α-amylase inhibition, and the SI extract standardized for sesamin.

In one embodiment, the composition of the present invention may include one or more of the CF extract, the SR extract, and the SI extract at a specific concentration. For example, the composition of the present invention contains one or more of the CF extract which is standardized to contain forskolin at a concentration of from 1% to 98%, the SR extract which is standardized to inhibit 50% of α-glucosidase at a concentration of from 0.1 to 200 μg/mg and inhibit 50% of α-amylase at a concentration of from 0.1 to 100 μg/mg, and the SI extract which is standardized to contain sesamin at a concentration of from 40% to 90%. It is further preferred that the CF extract is standardized to contain forskolin in the range of from 40% to 98%. It is further preferred that the SR extract is standardized to inhibit 50% of α-glucosidase at a concentration of from 0.5 to 150 μg/mg and inhibit 50% of α-amylase at a concentration of from 0.5 to 50 μg/mg. It is further more preferred that the SR extract is standardized to inhibit 50% of α-glucosidase at a concentration of from 1 to 75 μg/mg and inhibit 50% of α-amylase at a concentration of from 1 to 35 μg/mg. It is further preferred that the SI extract is standardized to contain sesamin in the range of from 60% to 80%. It is preferred that the CF extract, the SR extract, and the SI extract be contained in a proportion (weight ratio) of from 2 to 30%, from 0.25 to 3%, and from 0.025 to 0.3%, respectively. It is further preferred that the CF extract, the SR extract, and the SI extract be contained in a proportion of from 5 to 15%, from 0.5 to 1.5%, and from 0.05 to 0.15%, respectively. It is further more preferred that the CF extract, the SR extract, and the SI extract be contained in a proportion of 10%, 1%, and 0.1%, respectively.

Here, the *Sesamum indicum* extract may be extracted from any sesame seeds, such as white sesame seeds, black sesame seeds, gold sesame seeds, brown sesame seeds, and the like but the present invention is not limited thereto.

It is preferred that the composition of the present invention be stored in room temperature with a relative humidity of about 60 to 80%. It is further preferred that the composition of the present invention be stored in room temperature with a relative humidity of about 70%.

The composition of the present invention may be administered orally, sublingually, parenterally, or topically but preferably be administered orally. In case of oral administration, the composition of the present invention may be provided in the form of capsules, tablets, water dispersible powder or in the form of drink together with an appropriate vehicle. In case of topical use in the form of cream, lotion or transdermal application, the composition of the present invention is applied with an appropriate vehicle in concentration ranging from 0.1% to 15%. The vehicle may be any pharmaceutically acceptable vehicle. Such vehicle includes a coloring agent, a flavoring agent, a preservative, a stabilizer, an antioxidant, and the like but the present invention is not limited thereto.

In one embodiment of the present invention, the composition of the present invention is administered in a nutritionally and/or pharmacologically effective amount for diminishing viscera fat (including liver fat) and body fat due to sustained (prevention of tachyphylaxis) and safe inhibition (moderation of inhibition of pancreatic lipase activity) of pancreatic lipase activity.

The composition of the present invention may be administered in a daily dose from 10 to 2000 mg in a nutritionally and/or pharmacologically effective amount. It is preferred that the composition of the present invention be administered in a daily dose from about 832.5 to 1665 mg. It is preferred that the daily dose be divided into two or more individual doses. It is further preferred that the daily dose be divided into two or three individual doses. It is preferred that three individual doses be administered 15 minutes to 1 hour before a meal. It is further preferred that three individual doses be administered 30 minutes before a meal. In this case, IT is preferred that dose of one time is from 10 to 1000 mg. It is further preferred that dose of one time is from about 277.5 mg to about 555 mg.

It is preferred that the composition of the present invention be provided as dietary supplement in a daily oral dose of 5 mg/kg to 100 mg/kg of body weight. It is further preferred that the composition of the present invention be provided as dietary supplement in a daily oral dose of 12 mg/kg to 25 mg/kg of body weight.

Furthermore, the composition of the present invention may also be used as a single daily dose, e.g. as a maintenance dose. It is preferred that the maintenance dose be in the range of from 30.8 mg to 555 mg per day. It is further preferred that the maintenance dose be in the range of from 100 mg to 400 mg per day. It is most preferred that the maintenance dose be in the range of from 200 mg to 300 mg per day.

In one embodiment, the composition of the present invention is a combination of a biological response modifying dose of *Sesamum indicum* extract and *Coleus forskohlii* extract or *Salacia reticulata* extract. This can prevent excessive and non-physiological inhibition of pancreatic lipase activity and the potential side effects.

In another embodiment, the composition of the present invention is a combination of a clinically effective dose of *Coleus forskohlii* extract and a biologically negligible (subclinical) dose of *Salacia reticulata* extract, resulting in prevention of tachyphylaxis.

In the above embodiment, a preferred clinically effective dose of *Coleus forskohlii* extract is in the range of from 0.1 to 1000 µg/ml, a more preferred clinically effective dose of *Coleus forskohlii* extract is in the range of from 1 to 100 µg/ml, a preferred biologically negligible (subclinical) dose of *Salacia reticulata* extract is in the range of from 0.01 to 100 µg/ml, a more preferred biologically negligible (subclinical) dose of *Salacia reticulata* extract is in the range of from 0.1 to 10 µg/ml, a preferred biological response modifying dose of *Sesamum indicum* extract is in the range of from 0.1 to 1000 µg/ml, and a more preferred biological response modifying dose of *Sesamum indicum* extract is in the range of from 1 to 100 µg/ml.

By using the above administration method, the composition of the present invention is provided for safe and effective inhibition of pancreatic lipase without drawbacks and side effects of the current generation of pancreatic lipase inhibitors. The method of the present invention can prevent diminishing the mechanism of action of the composition of the present invention in aging population and prevent excessive and non-physiological inhibition of pancreatic lipase activity.

It is believed that the mechanism of action of the composition of the present invention, without being bound by any specific theory, inhibits postprandial ghrelin response manifested by decreased cravings for food. Ghrelin is a hormonal substance that is associated with increased plasma leptin levels. This combined action lowers production and secretion of pancreatic lipase. The composition of the present invention also interacts directly with pancreatic lipase and inhibits colipase preventing activation of the PTL enzyme.

The present invention also encompasses a method for producing the composition of the present invention from *Coleus forskohlii*, *Salacia reticulata*, and *Sesamum indicum*.

Hereinafter, a more specific description will be given of the present invention based on Examples. It should be noted that the present invention is not limited to the following Examples.

EXAMPLES

1. Preparation of the CF Extract

*Coleus forskohlii* root powder was extracted with 2 volumes of water at 60° C. for 2 hours. The spent material was dried and extracted through Super Critical Fluid Extraction (SCFE). The SCFE oleoresin was washed in 2 volumes of 70% ethanol (cane sugar ethanol) at 50° C. for 1 hour. The mixture was allowed to settle for 18 hours then was separated by siphoning the clear liquid layer from the top layer. The bottom layer was filtered through Nutche filter. The wet cake was dried at 65° C. under vacuum for 16 hours. The dried extract was pulverized through 0.5 mm mesh and analyzed for content of forskolin. Resulting product was blended with maltodextrin and 3% Aerosil to obtain desired concentration of forskolin.

2. Preparation of a Mixture of the CF Extract and the SR Extract

Next, the CF extract in desired strength, e.g. 10-98% was then combined with extract of *Salacia reticulata* roots.

*Salacia reticulata* root powder was extracted with 5 volumes of water at 70 to 80° C. The water extraction was repeated 3 times, and the resulting extract was filtered using 5 micron filter cloth. Clear filtrate was allowed to settle for 8 hours and separated by siphoning top layer and was concentrated under vacuum at 80° C. to 25 to 30% TDS (Total Dissolved Solids) concentration. The semi concentrated mass was then spray dried. The dried powder was pulverized through 0.5 mesh. Next, α-glucosidase inhibition activity and α-amylase inhibition activity were measured.

Measurement of α-Glucosidase Inhibition Activity

Measurement of α-glucosidase inhibition activity for standardizing the SR extract was performed by the following method.

Principle

By measuring the reducing sugar (Glucose) arising from hydrolysis of sucrose by α-glucosidase enzyme, isolated from small intestine of rat, α-glucosidase activity can be measured in-vitro.

Material

The material α-glucosidase was prepared as follows. Rats were sacrificed, and intestine was removed and chilled with ice cold 80 mM phosphate buffers (pH 7.0). The intestine was then cut open, the mucosa was scraped off with a piece of glass rod and homogenized in homogenizer with four volumes (v/v) of ice cold 80 mM phosphate buffer (pH 7.0). The sample tube was chilled with crushed ice during homogenization. Nuclei and large cell debris were removed by centrifugation at 2000 to 4000 rpm for 10 minutes and supernatant was aliquoted into 1.5 ml vials and stored at −20° C. This was α-glucosidase enzyme solution. Protein content measured by Biuret method was approximately 0.5 g/dl. The Biuret method was performed using Total protein estimation kit (B-0211, Span diagnostics).

The substrate was used which was dissolved in 80 mM phosphate buffer (pH 7.0) (RM3063, Himedia, India and stored at room temperature) sucrose, made in 37 mM.

The positive control was used in which acarbose (Glucobay) (Bayer Pharma, India and stored at room temperature) was dissolved in 5 µg/ml 80 mM phosphate buffer (pH 7.0).

The glucose reagent (India, the AGAPPE diagnostics company 11208102) was used.

Method

The α-glucosidase inhibition activity was measured by modification of the method disclosed in Vogel GH, Vogel WH (1997), Drug Discovery and Evaluation, Pharmacological assay, Springer-Verlag: Germany, 588-589. In brief, to 250 µl of 80 mM phosphate buffer including vehicle buffer, positive control, and test sample of various concentrations was added 50 µl of enzyme solution to obtain reaction mixture. The reaction mixture was mixed and pre-incubated at 37° C. for 30 minutes. Following pre-incubation, 500 µl of substrate (37 mM Sucrose) was added to the reaction mixture and the resulting reaction mixture was incubated at 37° C. for 20 minutes. The reaction was arrested by keeping the reaction mixture in boiling water bath for 2 minutes and then was cooled. To 50 µl of the reaction mixture was added 250 µl of glucose reagent and the resulting mixture was incubated at 25° C. for 10 minutes. The absorbance at 510 nm was measured using Molecular devices Versamax microplate reader. A control reaction was carried out without the test sample.

Inhibition rate (%) was calculated by the following formula:

Inhibition rate(%)=(absorbance(control)−absorbance (test sample))/absorbance(control)×100

$IC_{50}$ was calculated using log-proit analysis. Appropriate solvent and color corrections were made in case of colored samples and non-aqueous solutions.

Measurement of α-Amylase Inhibition Activity

The α-amylase inhibition activity for standardizing the SR extract was measured by the following method.

Principle

Pancreatic α-amylase hydrolyses the 2-chloro-4-nitrophenol α-D-maltotrioside (CNP-G3) to release 2-chloro-4-nitrophenol and form 2-chloro-4-nitrophenol α-D-maltoside (CNPG2), maltotriose and glucose. The rate of formation of the 2-chloro-4-nitrophenol can be measured at the absorbance of 405 nm.

Material

The used α-amylase (EC 3.2.1.1) was Type VI-B (From porcine pancreas) 500,000 units (15.8 units/mg solid at pH 6.9) A3176, Sigma, USA). α-amylase was used which was dissolved in 40 mM phosphate buffer (pH 6.9), made in 0.5128 units/ml.

The substrate, CNP-G3 reagent off-the-shelf, was used at a concentration of 2.3 mM (2-chloro-4-nitrophenol α-D-maltotrioside, AMF060CH, Chema Diagnostica, Italy, stored at 2 to 8° C.).

The positive control was used in which acarbose (Glucobay) (Bayer Pharma, India and stored at room temperature) was dissolved in 2.5 μg/ml 40 mM phosphate buffer (pH 6.9).

Method

The α-amylase inhibition activity was measured by modification of the method disclosed in Gella F J, Gubern G, Vidal R, Canalias F, (1997), Determination of total and pancreatic α-amylase in human serum with 2-chloro-4-nitrophenyl-α-D-maltotrioside as substrate. Clinica Chimica Acta 259, 147-160. In brief, to 60 μl of 40 mM phosphate buffer (pH 6.9) including vehicle buffer, positive control, and test sample was added 30 μl of enzyme solution (0.5128 units/ml) to obtain reaction mixture. The reaction mixture was mixed and pre-incubated at 37° C. for 10 minutes. Following pre-incubation, 125 μl of substrate (2.3 mM CNP-G3) was added to the reaction mixture and the resulting reaction mixture was incubated at 37° C. for 8 minutes. The absorbance at 405 nm was measured using Molecular devices Versamax microplate reader. A control reaction was carried out without the test sample.

Inhibition rate (%) was calculated by the following formula:

Inhibition rate(%)=(absorbance(control)−absorbance (test sample))/absorbance(control)×100

$IC_{50}$ was calculated using log-probit analysis. Appropriate solvent and color corrections were made in case of colored samples and non-aqueous solutions.

Based on the method described above, the SR extract was standardized to inhibit 50% of α-glucosidase at a concentration of from 1 to 75 μg/mg and inhibit 50% of α-amylase at a concentration of from 1 to 35 μg/mg.

3. Preparation of a Mixture of the CF Extract, the SR Extract, and the SI Extract The blend of the CF extract with the SR extract was then combined with *Sesamum indicum* seeds extract.

*Sesamum indicum* seeds were washed with water, dried and extruded to collect the oil. The oil was filtered through filter press and the clear oil was taken for extraction. Sesame oil was extracted with ethanol (cane sugar ethanol) at 75 to 80° C. for 2 hours. The mass was settled for an hour and layers were separated. The top layer contained SI material and was separated through a view glass through the bottom valve of the extractor. The bottom layer was subjected for 3 more extraction. The 4 extracts were concentrated to a thick paste at 70° C. under vacuum. The paste was kept for 7 days for aging. The Aged material was mixed with 2 volumes of sugar cane ethanol and filtered through Nutche filter. The wet cake was washed with 1.5 volumes of Ethanol and filtered. The obtained wet cake was mixed with 2 volumes of water, heated to 60° C. and filtered through Nutche filter. The wet cake was dried under vacuum at 65° C. The dried material was then charcolised by dissolving in 21 volume of ethanol. Five percent activated charcoal was added based on the dried weight. Charcolised mass was filtered through hyflow bed which was prepared over 2 micron filter cloth. Hyflow filtration was repeated for two times using new hyflow bed. The clear filtrate was concentrated to thick paste under vacuum at 65° C. Next, the thick paste was then dried for 3 to 4 hours under vacuum at 60 to 65° C. Dried material was milled through 0.5 mm and dried again at 70° C. under vacuum for 3 hours. Redried material was milled, sifted and packed after quality approval. The final product is standardized for 70% Sesamin content by HPLC.

4. Clinical Trial of the CF Extract

*Coleus forskohlii* (CF) extract which is the component of the invention standardized for 10% forskolin has been evaluated in a 6 week clinical trial with 15 volunteers (8 volunteers for test diet group (average age 41±4 years old, average body weight 77.5±11.4, and average BMI 27.2±0.9) and 7 volunteers for control diet group (average age 36±9 years old, average body weight 75.6±7.3 kg, and average BMI 27.5±1.4)). The randomized study subjects received either 250 mg×2 capsules of 10% the CF extract or 250 mg×2 capsules of matching placebo 30 minutes before breakfast, and 30 minutes before a dinner. Total daily intake of the CF extract/placebo was 1000 mg (4 capsules) for six weeks. There was no dietary or life style modification in course of the study.

5. Clinical Trial Result of the CF Extract Percentage Body Fat

The percentage of body fat for the CF extract group was statistically significantly lower at the completion of administration compared to the baseline (P<0.05). The percentage of body fat for the placebo group was statistically significantly higher (p<0.05) at the end of administration compared to the baseline values. The percent body fat in the CF extract group pre-administration was 34.1±4.2% and post-administration 33.5±4.4% vs. placebo pre-administration 35.0±6.6% and post-administration 35.9±6.5%. The fat content changes were measured with computerized tomographic scanning in various anatomic areas, were evaluated in 3 subjects from the CF extract group before and after 6 weeks of the regimen. The whole body fat, subcutaneous fat and central abdominal fat were diminished at the completion of the study compared to the baseline values. (see Table 1).

Table 1 shows the results of computerized tomographic scanning evaluating body fat content in various anatomic areas in 3 study subjects, before and after 6 weeks of treatment with *Coleus forskohlii* extract 250 mg×4 capsules a day.

TABLE 1

| BODY PART AND DIFFERENCE | MEASURE | PRE-TREATMENT | POST-TREATMENT |
|---|---|---|---|
| WHOLE BODY | cm$^2$ | 345.2 ± 59.7 | 330.1 ± 37.6 |
| HYPODERMAL | cm$^2$ | 212.9 ± 55.5 | 215.2 ± 45.3 |
| INTRAPERITONEAL (ABDOMINAL) | cm$^2$ | 132.3 ± 95.6 | 114 ± 73.5 |
| DIFFERENCE IN WHOLE BODY | cm$^2$ | — | −15.1 ± 22.8 |
| DIFFERENCE IN SUBCUTANEOUS | cm$^2$ | — | 2.3 ± 19.4 |
| DIFFERENCE IN ABDOMINAL | cm$^2$ | — | −17.4 ± 25.3 |

Body Weight

Numerically the CF extract group showed lower weight at the end of 6 weeks and in the placebo group the numerical weight was increased at the end of 6 weeks as compared to the respective baseline values. The CF extract group pre-trial body weight was 77.5±12 kg and post-trial body weight was 76.6±12.1 kg, whereas the placebo pre-trial body weight was 75.5±7.2 kg, and the post-trial body weight was 76±7.4 kg.

Waist Circumference

Waist circumference in the CF extract group was numerically lower compared to the baseline values, i.e. pre-trial was 93.9±7.8 cm and post-trial was 93.2±8 cm. In the placebo group, there was numerical increase in circumference at the end of trial comparing it to baseline values, i.e., pre-trial waist circumference was 92.1±7.1 cm and post-trial was 92.4±7.1 cm. Similar pattern of change to waist circumference was recorded in hip circumference, i.e., in the CF extract group, pre-trial was 101±2.9 cm and post-trial 100.1±3 cm; in the placebo group, pre-trial hip circumference was 100.2±3.4 cm and post-trial was 100.4±3.3 cm.

Blood Lipids

The blood lipid laboratory data showed trends in the CF extract and placebo receiving groups, i.e., the total cholesterol in the CF extract group was decreased from baseline value of 213±28 mg/dl to post-trial value of 200±15 mg/dl. The total cholesterol in the placebo receiving group was increased from baseline value of 218±38 mg/dl to post trial value of 221±35 mg/dl. The triglyceride in the CF extract group was decreased from pre-trial value of 137±69 mg/dl to post-trial value of 120±74 mg/dl. The triglyceride value in the placebo receiving group was increased from the baseline value of 98±33 mg/dl to post-trial value of 109±54 mg/dl.

Caloric Intake

The effects of 6 weeks administration of the CF extract on caloric intake of food were compared to the placebo group. In the placebo group, caloric intake was increased by approximately 700 kcal by the end of 6 weeks, whereas in the CF extract group, caloric intake was decreased by approximately 300 kcal by the end of 6 weeks. The difference between the CF extract and placebo groups caloric intake was statistically significant ($p<0.05$, see Table 2). The significantly decreased caloric intake in the CF extract group vs. placebo group indicates a safety effect of the present invention, which shows an unexpected finding in view of current generation pancreatic lipase inhibitors showing tendency to increase levels of appetite (Non-Patent Document 3).

Table 2 shows the appetite effect measured by calorie intake in *Coleus forskohlii* extract or placebo receiving subjects for 6 weeks.

TABLE 2

| PARAMETERS | MEASURE | STUDY GROUPS | PRE-TEST | POST-TEST |
| --- | --- | --- | --- | --- |
| FOOD INTAKE | Kcal | CF EXTRACT | 5519 ± 1341 | 5222 ± 1301 |
| | | PLACEBO | 5827 ± 1535 | 6527 ± 1210 |

6. Inhibition of Pancreatic Lipase In Vitro

The in vitro study evaluated three components of present invention, i.e., *Coleus forskohlii, Salacia reticulata*, and *Sesamum indicum* for their properties inhibiting pancreatic lipase activity.

(1) Test Material

The test substances used were 98% *Coleus forskohlii* extract (lot number: OL110048), 40% *Coleus forskohlii* extract (lot number: BAJ/COL 40/110211), *Salacia reticulata* extract (lot number: BAJ/SRE/100816), 70% white *Sesamum indicum* extract (lot number: BAJ/SME/100220), and Tarragon extract (lot number: 0708/908005). These were stored at room temperature.

The reagents used were porcine pancreatic lipase (lot number: 020M1589V, SIGMA), MOPS (lot number: BCBB5948, SIGMA), EDTA.2Na.2H$_2$O (lot number: BCBB4814, SIGMA), Trizma (registered trademark) Base (lot number: 0001414448, SIGMA), calcium chloride.2H$_2$O (lot number: BCBC3028V, SIGMA), N,N-dimethylformamide (lot number: 60796HM, SIGMA), 4-nitrophenyl butyrate (lot number: 029K5217V, SIGMA), hydrochloric acid (lot number: KWM6937, Wako Pure Chemical Industries), and Orlistat (lot number: 0422583-6, Cayman Chemical Company).

The measurement instrument used was multi-mode microplate reader Mithras LB 940 (BERTHOLD TECHNOLOGIES GmbH & Co. KG).

(2) Test Method

Method for the Preparation of Reagents

The reagents were prepared with reference to the report of Lee et al (Eun Mi Lee, Seung Sik Lee, Byung Yeoup Chung, Jae-Young Cho, In Chul Lee, So Ra Ahn, Soo Jeung Jang and Tae Hoon Kim, Pancreatic Lipase Inhibition by C-Glycosidic Flavones Isolated from Eremochloa ophiuroides, Molecules 2010, 15, 8251-8259; doi: 10.3390/molecules 15118251) and the report of Lunder et al (Lunder, M., T. Bratkovic, S. Kreft, and B. Strukelj. 2005. Peptide inhibitor of pancreatic lipase selected by phage display using different elution strategies, J. Lipid Res. 46: 1512-1516. DOI 10.1194/jlr. M500048-JLR200). Tris buffer (pH 6.8) of 100 mmol/L of Tris-HCl containing 5 mmol/L of calcium chloride and 1 mmol/L of EDTA.2Na was prepared. The porcine pancreatic lipase was suspended by adding aqueous solution of 10 mmol/L of MOPS to obtain about 1000 unit/mL of a porcine pancreatic lipase solution. To 30 µL of a porcine pancreatic lipase solution was added 850 µl of a Tris buffer to obtain an enzyme solution. To 4-nitrophenyl butyrate was dissolved by adding N,N-dimethylformamide to prepare 40 mmol/L of a substrate solution. N,N-dimethylformamide and Tris buffer were mixed in a ratio of 1:4 to obtain the test substance preparation solution.

Method for the Preparation of the Test Substances

The test substances were dissolved into the test substance preparation solution. After preparation of the concentration of 1000 µg/mL, the resulting solution was diluted 10-fold in sequence. The test substances were prepared to a concentration of 100, 10, and 1 µg/mL. These were used as specimen in these tests, only the test substance preparation solution was used in the control.

Measurement Method

Measurement was performed with reference to the reports of Lee et al and Lunder et al (1, 2). In a nutshell, 100 µL of a specimen (n=2) and 880 µL of an enzyme solution were added to a microplate, and the resulting microplate was incubated for 15 minutes at 37° C. After completion of incubation, 20 µL of the substrate solution was added and then the enzymatic reaction was started at 37° C. After start of the enzymatic reaction, the measurement of absorbance was continued for up to 15 minutes after every minute at 405 nm.

As a result, the degrees to which these three extracts inhibit pancreatic lipase activity were different. This fact is to provide new knowledge in order to safely and effectively inhibit pancreatic lipase activity.

Safe Inhibition of Pancreatic Lipase

A safety mechanism to prevent excessive inhibition of pancreatic lipase is the primary feature of the method of the present invention. *Sesamum indicum* extract prevents side effects of excessive pancreatic lipase inhibition by dose dependent control of this mechanism. In in vitro experiments, stand alone *Sesamum indicum* extract (*Sesamin*) has shown dual action depending on low and high dose of the extract (see FIG. 1 and FIG. 2).

In a low dose range (0.1 μg/ml and 1 μg/ml), *Sesamum indicum* extract statistically significantly outperforms *Coleus forskohlii* extract (*C. Forskohlii*) and *Salacia reticulata* extract (*Salacia*), inhibiting pancreatic lipase. However, in a higher dose range (10 μg/ml and 100 μg/ml), *Sesamum indicum* extract becomes statistically significantly less effective than equivalent doses of *Coleus forskohlii* extract and *Salacia reticulata* extract inhibiting pancreatic lipase.

Figure 2:
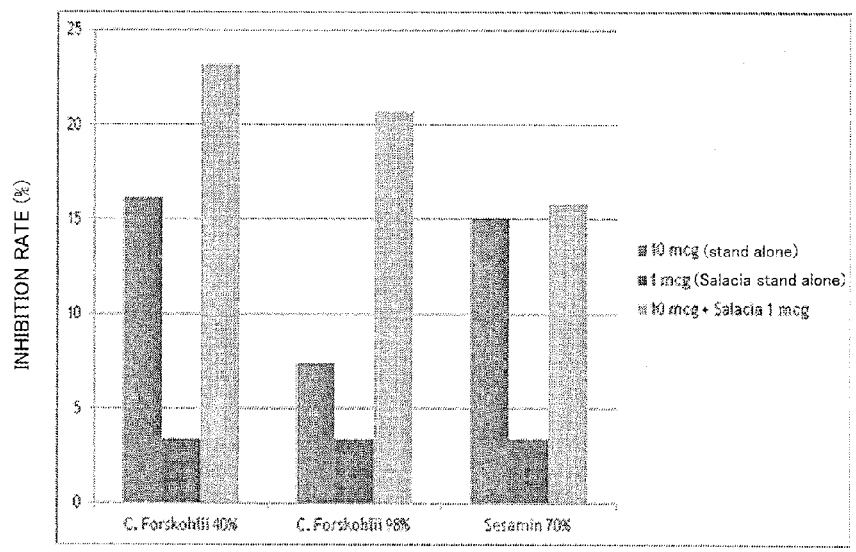
FIG. 2 is a graph illustrating the inhibition rate of pancreatic lipase activity when the SR extract (*Salacia*) and the CF extract (*C. Forskohlii* 98% or 40%) or the SR extract (*Salacia*) and the SI extract (*Sesamin* 70%) are used in combination.

Unexpectedly, upon addition of 1 μg/ml *Sesamum indicum* extract to 10 μg/ml 98% *Coleus forskohlii* extract resulted in only 9.6% inhibition of pancreatic lipase, as opposed to mathematically calculated 23.4% inhibition from sum of % inhibition afforded by either of standalone compounds (see FIG. 1, Table 3, and Table 4). The biological response to modify the effect of *Sesamum indicum* extract is a new and useful in the sense of preventing the potential side effects and inhibition of non-physiological in excess of pancreatic lipase activity.

Table 3 represents the inhibition of pancreatic lipase in a dose-dependent manner in vitro according to components of the present invention.

TABLE 3

| Group | Focal conc. (μg/mL) | OD at 405 nm $OD_0$ | OD at 405 nm $OD_{15}$ | ΔOD ($OD_{15}$− $OD_0$) | Mean of ΔOD | Inhibition ratio (%) |
|---|---|---|---|---|---|---|
| Control | 0 | 0.395 | 2.434 | 2.036 | 2.102 | — |
|  |  | 0.378 | 2.535 | 2.367 |  |  |
| Coleus Forskohlii Extract 98% | 0.1 | 0.239 | 2.242 | 2.003 | 2.000 | 4.8 |
|  |  | 0.224 | 2.221 | 1.997 |  |  |
|  | 1 | 0.258 | 2.233 | 1.975 | 1.998 | 4.8 |
|  |  | 0.238 | 2.259 | 2.021 |  |  |
|  | 10 | 0.200 | 2.118 | 1.018 | 1.915 | 7.4 |
|  |  | 0.222 | 2.199 | 1.972 |  |  |
|  | 100 | 0.168 | 0.736 | 0.368 | 0.535 | 74.5 |
|  |  | 0.169 | 0.671 | 0.502 |  |  |
| Coleus Forskohlii Extract 40% | 0.1 | 0.200 | 2.123 | 1.023 | 1.953 | 7.1 |
|  |  | 0.263 | 2.246 | 1.983 |  |  |
|  | 1 | 0.239 | 2.180 | 1.941 | 1.924 | 8.4 |
|  |  | 0.300 | 2.207 | 1.507 |  |  |
|  | 10 | 0.205 | 1.971 | 1.366 | 1.364 | 16.1 |
|  |  | 0.256 | 2.017 | 1.761 |  |  |
|  | 100 | 0.384 | 1.575 | 1.191 | 1.205 | 42.3 |
|  |  | 0.411 | 1.630 | 1.219 |  |  |
| *Salacia reticulata* Extract | 0.1 | 0.277 | 2.255 | 1.978 | 2.040 | 2.9 |
|  |  | 0.258 | 2.360 | 2.162 |  |  |
|  | 1 | 0.277 | 2.317 | 2.010 | 2.030 | 3.4 |
|  |  | 0.237 | 2.256 | 2.019 |  |  |
|  | 10 | 0.234 | 1.968 | 1.234 | 1.750 | 16.7 |
|  |  | 0.228 | 1.994 | 1.766 |  |  |
|  | 100 | 0.410 | 1.393 | 0.983 | 0.975 | 53.6 |
|  |  | 0.375 | 1.342 | 0.967 |  |  |

Table 4 represents the inhibition of pancreatic lipase in vitro by a combination of the components of the present invention.

TABLE 4

| Group | Final conc. (μg/mL) | OD at 405 nm $OD_0$ | OD at 405 nm $OD_{15}$ | ΔOD ($OD_{15}$-$OD_0$) | Mean of ΔOD | Inhibition ratio (%) |
|---|---|---|---|---|---|---|
| Control | 0 | 0.304 | 2.443 | 2.139 | 2.138 | — |
|  |  | 0.365 | 2.502 | 2.137 |  |  |
| *Coleus forskohlii* Extract 40% + | 10 | 0.301 | 2.172 | 1.871 | 1.839 | 14.0 |
| White Sesamin Extract 70% | +1 | 0.245 | 2.052 | 1.807 |  |  |
| *Coleus forskohlii* Extract 40% + | 10 | 0.292 | 1.912 | 1.620 | 1.642 | 23.2 |
| *Salacia Reticulata* Extract | +1 | 0.35 | 2.014 | 1.664 |  |  |
| *Coleus forskohlii* Extract 98% + | 10 | 0.288 | 2.192 | 1.904 | 1.933 | 9.6 |
| White Sesamin Extract 70% | +1 | 0.343 | 2.304 | 1.961 |  |  |
| *Coleus forskohlii* Extract 98% + | 10 | 0.358 | 2.028 | 1.670 | 1.695 | 20.7 |
| *Salacia Reticulata* Extract | +1 | 0.332 | 2.052 | 1.720 |  |  |

TABLE 4-continued

| Group | Final conc. (µg/mL) | OD at 405 nm | | ΔOD (OD$_{15}$-OD$_0$) | Mean of ΔOD | Inhibition ratio (%) |
|---|---|---|---|---|---|---|
| | | OD$_0$ | OD$_{15}$ | | | |
| White Sesamin Extract 70% + | 10 | 0.282 | 2.067 | 1.785 | 1.800 | 15.8 |
| Salacia Reticulata Extract | +1 | 0.334 | 2.149 | 1.815 | | |

These values were measured before the enzyme reaction was proceeded (t = 0).
These values were measured at the enzyme reaction was finished (t = 15).
Inhibition ratio was calculated from next formula.

$$\text{Inhibition ratio (\%)} = \left(1 - \frac{\text{Mean of } \Delta\text{OD after the sample was applied}}{\text{Mean of } \Delta\text{OD in Control}}\right) \times 100$$

Prevention of Tachyphylaxis

The *Coleus forskohlii* extract and the *Salacia reticulata* extract work in a synergistic manner for the prevention of tachyphylaxis and for the mechanism to be resistant to decrease of biological activity of *Coleus forskohlii* extract and *Salacia reticulata* extract for inhibiting pancreatic lipase activity due to repeated use and over time and with increased age of patients. This fact is a new and useful knowledge to safely and effectively inhibit pancreatic lipase activity.

Synergistic Inhibition of Pancreatic Lipase

The synergistic action of the present invention can be illustrated by in vitro experiment inhibiting pancreatic lipase by combining biologically inactive dose (1 µg/ml) of *Salacia reticulata* extract with the suboptimal dose (10 µg/ml) of *Coleus forskohlii* extract (see Table 4). The synergistic action of the CF extract with the SR extract resulted in 20.7% inhibition of pancreatic lipase activity comparing to only 10.8% inhibition calculated from addition of % inhibition values for the CF extract and the SR extract stand alone. Therefore, combination of biologically inactive dose of *Salacia reticulata* with biologically suboptimal dose of *Coleus forskohlii* resulted in unexpected synergistic action, which is an inventive step and basis of efficacy of the present invention in body weight management.

7. The Results of Clinical Trials and In Vitro Tests

The clinical evidence revealed in tests of six weeks was that the CF extract has diminished viscera fat and blood triglyceride. By combining the results of in vitro inhibition of pancreatic lipase activity with this discovery, it was found for the first time that the CF extract inhibits pancreatic lipase. The discovery of the activity of the CF extract for inhibiting pancreatic lipase is novel. In particular, the discovery shows the exact opposite of the findings (Non-Patent Document 6) of a rapid increase in synthesis rate of lipase and colipase upon incubation of pancreatic tissue with diterpene forskolin.

What is claimed is:

1. A method of reducing body fat in a human in need thereof consisting essentially of administering a therapeutically effective amount of a composition of a mixture of *Coleus forskohlii* extract, *Salacia reticulata* extract, and *Sesamum indicum* extract to the human in need thereof to reduce the body fat in the human.

2. The method of claim 1, wherein the *Coleus forskohlii* extract is standardized to contain folskolin at a concentration of from 1% to 98%.

3. The method of claim 1, wherein the *Salacia reticulata* extract is standardized to inhibit 50% of α-glucosidase at a concentration of from 0.1 to 200 µg/mg and inhibit 50% of α-amylase at a concentration of from 0.1 to 100 µg/mg.

4. The method of claim 1, wherein the *Sesamum indicum* extract is standardized to contain sesamin at a concentration of from 40% to 90%.

5. The method of claim 1, wherein the *Coleus forskohlii* extract is standardized to contain forskolin at a concentration of from 1% to 98%, the *Salacia reticulata* extract is standardized to inhibit 50% of α-glucosidase at a concentration of from 0.1 to 200 µg/mg and inhibit 50% of α-amylase at a concentration of from 0.1 to 100µg/mg, the *Sesamum indicum* extract is standardized to contain sesamin at a concentration of from 40% to 90%, and the *Coleus forskohlii* extract, the *Salacia reticulata* extract, and the *Sesamum indicum* extract are contained in a proportion of from 2 to 30%, from 0.25 to 3%, and from 0.025 to 0.3%, respectively.

6. The method of claim 1, wherein the *Coleus forskohlii* extract is standardized to contain forskolin at a concentration of from 1% to 98%, the *Salacia reticulata* extract is standardized to inhibit 50% of α-glucosidase at a concentration of from 0.1 to 200 µg/mg and inhibit 50% of α-amylase at a concentration of from 0.1 to 100 µg/mg, and the *Coleus forskohlii* extract and the *Salacia reticulata* extract are contained in an amount of from 0.1 to 10 µg/ml and from 1 to 20 µg/ml, respectively.

7. The method of claim 1, wherein the composition is administered in a range of from 10 to 2000 mg per day.

* * * * *